United States Patent
Frigg et al.

(10) Patent No.: US 9,107,716 B2
(45) Date of Patent: Aug. 18, 2015

(54) FLEXIBLE MAXILLO-MANDIBULAR FIXATION DEVICE

(75) Inventors: Robert Frigg, Langendorf (CH); Jens Richter, Oberdorf (CH); Samuel Leuenberger, Oberdorf (CH); Carl Peter Cornelius, Munich (DE); Ross Jonathan Hamel, West Chester, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 425 days.

(21) Appl. No.: 12/952,656

(22) Filed: Nov. 23, 2010

(65) Prior Publication Data

US 2011/0152946 A1  Jun. 23, 2011

Related U.S. Application Data (60) Provisional application No. 61/263,542, filed on Nov. 23, 2009.

(51) Int. Cl.
*A61B 17/56* (2006.01)
*A61B 17/80* (2006.01)
*A61F 5/058* (2006.01)

(52) U.S. Cl.
CPC ......... *A61B 17/8071* (2013.01); *A61F 5/05891* (2013.01); *A61B 17/8085* (2013.01)

(58) Field of Classification Search
USPC ........ 433/7, 10, 18–19; 606/70–71, 280–285, 606/300, 328, 902–903, 905, 906
See application file for complete search history.

(56) References Cited

U.S. PATENT DOCUMENTS

| | | | | |
|---|---|---|---|---|
| 1,638,006 | A * | 8/1927 | Aderer | 602/5 |
| 1,797,481 | A | 3/1931 | Preston | |
| 2,481,177 | A | 9/1949 | Toflemire | |
| 2,502,902 | A | 4/1950 | Tofflemire | |
| 2,580,821 | A * | 1/1952 | Toufick | 606/282 |
| 3,474,779 | A | 10/1969 | Wall | |
| 4,230,104 | A | 10/1980 | Richter | |
| 4,651,724 | A * | 3/1987 | Berentey et al. | 606/284 |
| 4,904,188 | A | 2/1990 | Baurmash | |
| 4,959,065 | A * | 9/1990 | Arnett et al. | 606/86 B |
| 5,074,865 | A * | 12/1991 | Fahmy | 606/54 |
| 5,250,048 | A * | 10/1993 | Gundolf | 606/297 |
| 5,468,242 | A * | 11/1995 | Reisberg | 606/285 |
| D366,114 | S * | 1/1996 | Ohata | D24/155 |
| 5,690,631 | A * | 11/1997 | Duncan et al. | 606/281 |

(Continued)

FOREIGN PATENT DOCUMENTS

| EP | 0654250 | 5/1995 |
|---|---|---|
| WO | WO 99/05982 | 2/1999 |

(Continued)

*Primary Examiner* — Christian Sevilla
(74) *Attorney, Agent, or Firm* — Baker & Hostetler LLP (57) ABSTRACT

A system for achieving maxillo-mandibular fixation includes a bone fixation device including a bone fixation body formed from a plurality of links. The links define corresponding crests and valleys so as to impart flexibility into the bone fixation body. Thus, the bone fixation body can be aligned with the dental arch of the mandible and maxilla as necessary, and subsequently fastened to the underlying bone. Each bone fixation device includes at least one securement location on the fixation body that can attach to a securement device, such that the securement device fixes or stabilizes the mandible and the maxilla with respect to each other.

13 Claims, 7 Drawing Sheets

(56) References Cited

U.S. PATENT DOCUMENTS

| | | | |
|---|---|---|---|
| 5,752,958 A | 5/1998 | Wellisz | |
| 5,779,707 A * | 7/1998 | Bertholet et al. | 606/75 |
| 5,984,925 A * | 11/1999 | Apgar | 606/284 |
| 6,086,365 A | 7/2000 | Fields | |
| 6,093,188 A * | 7/2000 | Murray | 606/282 |
| 6,106,544 A | 8/2000 | Brazeau | |
| 6,120,288 A | 9/2000 | Deslauriers | |
| 6,257,884 B1 | 7/2001 | Chang | |
| 6,471,706 B1 * | 10/2002 | Schumacher et al. | 606/70 |
| 2004/0030388 A1 * | 2/2004 | Null et al. | 623/17.11 |
| 2005/0192675 A1 * | 9/2005 | Robinson | 623/23.46 |
| 2008/0255620 A1 * | 10/2008 | Strauss et al. | 606/297 |
| 2009/0148804 A1 * | 6/2009 | Marcus | 433/7 |
| 2010/0179552 A1 * | 7/2010 | Wolter | 606/71 |
| 2011/0152951 A1 | 6/2011 | Baker | |

FOREIGN PATENT DOCUMENTS

| | | |
|---|---|---|
| WO | WO 2004/045389 | 6/2004 |
| WO | WO 2009/055537 | 4/2009 |
| WO | WO 2010/025263 | 3/2010 |

* cited by examiner

FLEXIBLE MAXILLO-MANDIBULAR FIXATION DEVICE

CROSS-REFERENCE TO RELATED APPLICATIONS

This patent application claims priority to U.S. provisional patent application No. 61/263,542, filed Nov. 23, 2009, which is incorporated herein by reference in its entirety.

BACKGROUND

The fixation or stabilization of the upper and lower dental occlusal arches to each other is known as intermaxillary fixation (IMF) and also known as maxillo-mandibular fixation (MMF). MMF has historically been included in the treatment of fracture, orthognathic, and reconstructive jaw procedures. Various methods for achieving MMF are known in the art.

Circumdental wiring techniques include metallic wires that are placed around one or more teeth and then twisted in various methods to secure the teeth. Wires or twisted pairs of wires can form cables and be twisted to each other to stabilize the dental arch. Loops formed on mandibular teeth can be wired to loops formed around maxillary teeth in order to stabilize the top dentition to the bottom dentition. While the materials used in circumdental wiring are relatively inexpensive, the technique is tedious and time consuming. The wires also can interfere with dental hygiene.

Another conventional technique includes arch bars that are used in combination with wiring. Specifically, a metal bar is preformed to correspond with the curvature of the dental arch. Wires are then passed around the teeth and over the bar, and then twisted to the bar. This is performed at multiple locations along the bar to provide stability around the dental arch. Since the bars typically have bent or formed hooks on them for securing wire, the hooks can be used for wiring the upper arch bar to the lower arch bar. Elastic bands can also be used to fix the upper arch bar to the lower arch bar. Unfortunately, this technique is time consuming, and interferes with dental hygiene.

Another conventional technique involves placing a plurality of screws in the mandible or maxilla in regions that avoid the tooth roots. The screw heads may contain through holes. The screw head serves as an area around which wires may be wrapped, and the holes can facilitate the passage of wire through the heads. Thus, wires may be secured to adjoining sets of screws to provide MMF. This system unfortunately suffers from a lack of overall structural stability which can be necessary, for instance, when addressing fractures around the teeth.

SUMMARY

In accordance with one embodiment, a bone fixation system includes first and second bone fixation devices. The first bone fixation device includes a first fixation body having a first securement location and a first attachment location. The first bone fixation device also includes a bone fastener configured to be embedded into an underlying first bone at the first attachment location, thereby attaching the first fixation body to the first bone. The second bone fixation device includes a second fixation body having a second securement location and a second attachment location. The second bone fixation device also includes a bone fastener configured to be embedded into an underlying second bone at the second attachment location, thereby attaching the second fixation body to the second bone. The first and second securement locations are configured to engage with a securement device that secures the first and second bone fixation devices with respect to each other.

BRIEF DESCRIPTION OF THE DRAWINGS

The foregoing summary, as well as the following detailed description, is better understood when read in conjunction with the appended drawings. For the purpose of illustrating the maxillo-mandibular fixation device and related method thereof, there is shown in the drawings exemplary embodiments; however, the maxillo-mandibular fixation device and related methods are not limited to the specific embodiments and methods disclosed. Like reference numerals refer to corresponding parts throughout the several embodiments of the drawings, in which.

DETAILED DESCRIPTION OF ILLUSTRATIVE EMBODIMENTS

For convenience, the same or equivalent elements in the various embodiments illustrated in the drawings have been identified with the same reference numerals. Certain terminology is used in the following description for convenience only and is not limiting. The words "right", "left", "upper," and "lower" designate directions in the drawings to which reference is made. The words "inward", "inwardly", "outward", "outwardly," "upward," "upwardly," "downward," and "downwardly" refer to directions toward and away from the geometric center of the device and/or designated parts thereof. The terminology intended to be non-limiting includes the above-listed words, derivatives thereof and words of similar import.

Figure 1:
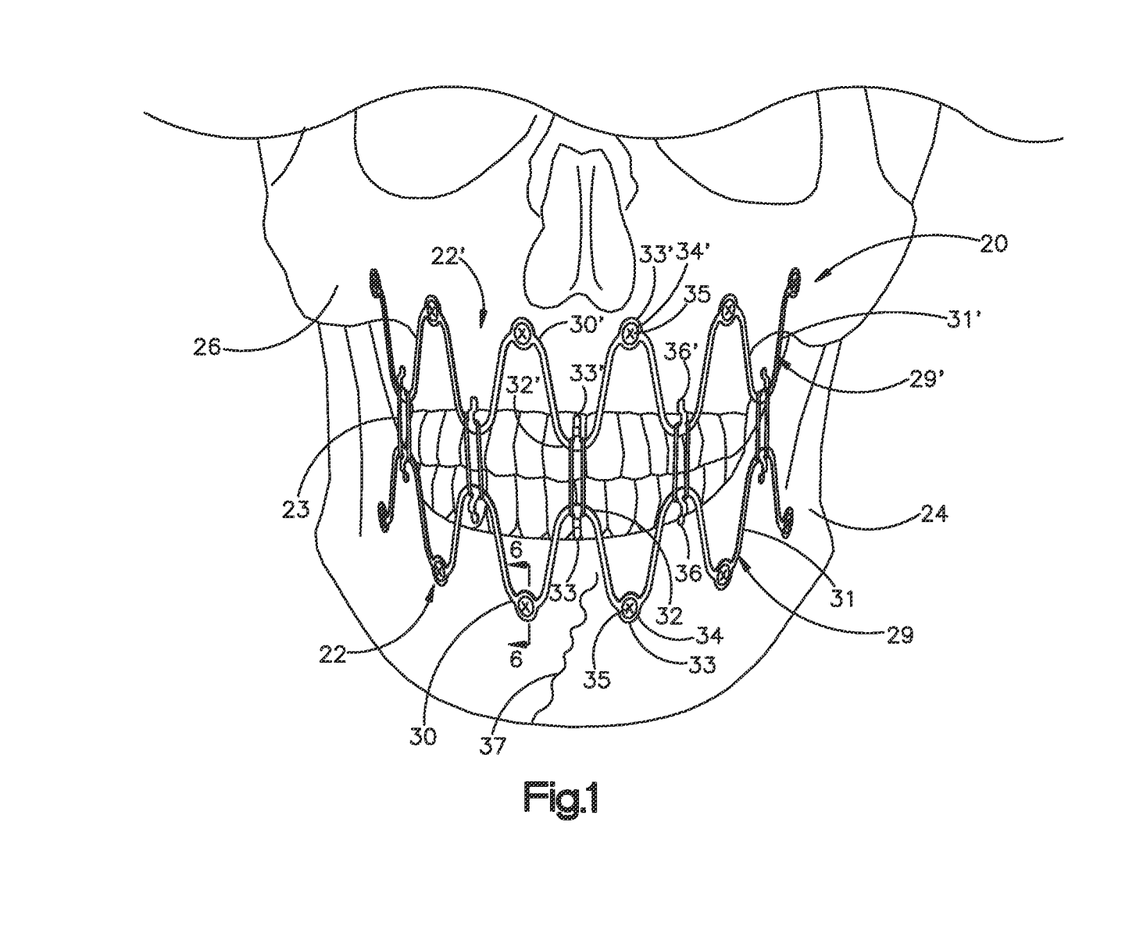
FIG. 1 is a perspective view of a maxillo-mandibular fixation system including a pair of fixation devices attached to the maxilla and mandible of a patient, and secured together.
Figures 2A, 2B:
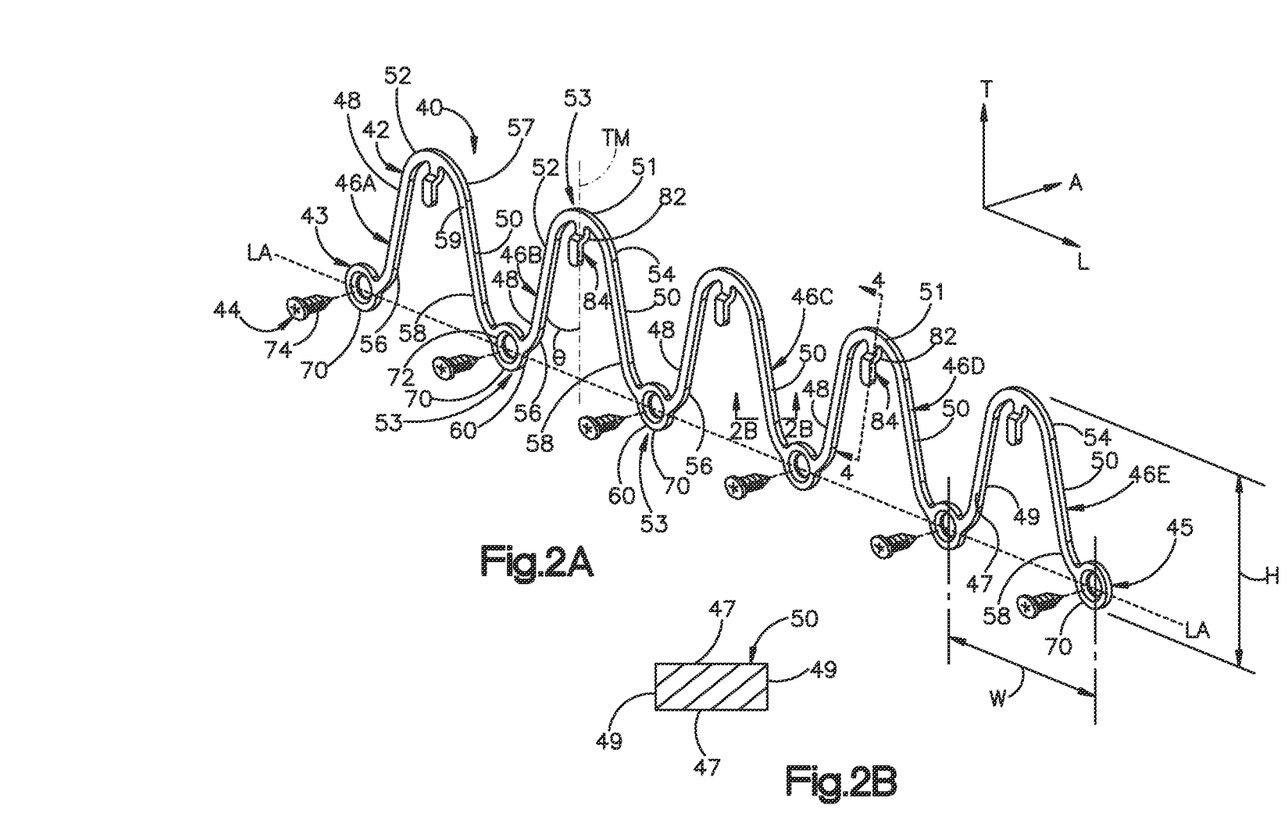
FIG. 2A is a perspective view of a bone fixation body constructed in accordance with one example embodiment in a neutral configuration.
FIG. 2B is a sectional elevation view of the fixation device illustrated in FIG. 2A taken along the line 2B-2B.

Referring initially to FIGS. 1 and 2A-B, a bone fixation, or stabilization, system 20 is configured to provide maxillomandibular fixation (MMF) for assisting the repairing of an injury to the maxillo-mandibular region. For instance, when the mandible 24 and/or maxilla 26 is fractured at a fracture location 37, it is desirable to stabilize the broken bone segments by fixing or stabilizing the maxilla and the mandible relative to each other. The fixation system 20 includes a pair of fixation devices 22 and 22', including bone fixation bodies 29 and 29', one or more fasteners 35 that attach each fixation body 29 and 29' to underlying bone, and one or more securement devices 23 that connect, or secure the fixation devices 22 and 22' to each other. The fasteners 35 can include bone screws or any other type of fastener suitable for attaching the fixation bodies 29 and 29' to underlying bone. Thus, the fixation devices 22 and 22' can be secured to the mandible 24 and the maxilla 26, respectively, of a patient. The suitable securement device 23 can secure the fixation bodies 29 and 29' to each other, thereby fixing the mandible 24 and the maxilla 26 with respect to relative movement.

Specifically, each fixation body 29 and 29' includes a respective plurality of flexible links 31 and 31' extending between a respective plurality of longitudinally spaced interfaces 33 and 33'. The pluralities of flexible links 31 and 31' extend upwardly and downwardly in an alternating pattern between the interfaces 33 and 33', thereby defining respective pluralities of valleys 30 and 30' and crests 32 and 32' between opposed ends of the fixation bodies 29 and 29'. The interfaces 33 and 33' defined at respective valleys 30 and 30' and crests 32 and 32' can be configured as connection or attachment locations. In the illustrated configuration, the interfaces 33 and 33' at the valleys 30 and 30' are configured as attachment locations having apertures 34 and 34', respectively. The apertures 34 and 34' can be configured to receive the fasteners 35. For example, the apertures 34 and 34' of the illustrated configuration are threaded so as to provide screw holes that receive fasteners 35 in the form of bone screws. Accordingly, the valleys 30 and 30' are configured as attachment locations that can be attached to underlying bone, for instance via the bone screws. The interfaces 33 and 33' at the crests 32 and 32' are configured as connection, or securement locations which can be secured to each other to in turn secure the fixation devices 22 and 22' with respect to each other. In the illustrated configuration, the interfaces 33 and 33' at the crests 32 and 32' are defined as securement locations having tangs 36 and 36' that extend outwardly from the crests 32 and 32' in a direction generally towards and in between the immediately adjacent valleys 30 and 30', respectively. The tangs 36 and 36' can be configured to receive a securement device, for instance the securement device 23, so as to secure the tangs 36 and 36' to each other. The securement device 23 can be provided as a suitable wire, elastic band, or any other alternative securement apparatus as desired.

The mandibular and maxillo fixation devices 22 and 22' can be identically or substantially identically constructed from a bone fixation device 40 (see FIG. 2A), and oriented as desired when implanted into the mandible 24 and maxilla 26 of a patient to provide the fixation devices 22 and 22'. Thus, the vertical orientations of the fixation devices 22 and 22' are inverted with respect to each other in the illustrated configuration. In particular, the mandibular fixation device 22 is oriented such that the plurality of crests 32 are positioned above the plurality of valleys 30, and the maxillo fixation device 22' is oriented such that the plurality of crests 32' is positioned below the plurality of valleys 30'. The maxillomandibular fixation system 20 will now be described with reference to the bone fixation device 40 as illustrated in FIG. 2A.

The bone fixation device 40 is illustrated as oriented in a vertical plane defined by a longitudinal direction "L" and transverse direction "T" that is perpendicular to the longitudinal direction, and has a thickness in a lateral direction "A" that is perpendicular to the longitudinal and transverse directions L and T, respectively. The bone fixation device 40 is elongate along the longitudinal direction L before the fixation device 40 is curved, bent, or otherwise configured to align with, for instance, the mandible or maxilla prior to implantation. Thus, while the description of the bone fixation device 40 is made with reference to the illustrated configuration of the fixation device 40, the description applies equally to orientations achieved when the fixation device 40 is configured for implantation, for instance, in the maxilla or mandible of a patient.

Unless otherwise specified herein, the terms "lateral," "longitudinal," and "transverse" are used to describe the orthogonal directional components of the bone fixation device 40 and its components as illustrated in FIG. 2A. The terms "inner," "outer," and derivatives thereof with respect to a specified directional component are used herein with respect to a given apparatus to refer to directions along the directional component toward and away from the center of the apparatus, respectively.

It should be appreciated that while the longitudinal and transverse directions are illustrated as extending along a vertical plane, and that the lateral direction is illustrated as extending along a horizontal plane, that the planes that encompass the various directions may differ during use, depending, for instance, on the desired orientation of the bone fixation device 40 when implanted in a patient. Accordingly, while certain directional terms are used herein to describe the bone fixation device 40 as illustrated merely for the purposes of clarity and convenience, it should appreciated that these orientations may change during use.

Therefore, while the bone fixation device 40 is described with respect to an orientation such that its base (i.e., its valleys) is disposed below its crest (i.e., its crests), it can be subsequently oriented as desired (for instance with the base disposed above the crest when providing the maxillo fixation device 22') when implanted in the patient. It should thus be understood that while the bone fixation device 40 is described in its illustrated orientation with reference to implantation in the mandible 24, it can alternatively be implanted in the maxilla 26 or any other desired bone structures that are to be fixed relative to each other.

With continuing reference to FIG. 2A, the bone fixation device 40 includes a flexible bone fixation body 42, which can also be referred to as a fixation plate or a fixation body, and a plurality of fasteners 44 configured to attach the fixation body 42 to underlying bone. The fixation body 42 is illustrated as defining opposed first and second longitudinally outer ends 43 and 45, respectively, and opposed inner and outer lateral surfaces 57 and 59. The inner surface 57 faces the gum surrounding the bone structure to which the fixation body 42 is attached, and the outer surface 59 faces a direction opposite the inner surface 57. The fixation body 42 includes a plurality of sequential links 46 A-E that can be integrally connected as illustrated, or can alternatively be discreetly attached to each other. The links 46A and 46E define outer links, while the links 46B-D define inner links disposed between the outer links 46A and 46E. In one embodiment, the fixation body 42 is formed by wire electrical discharge machining (wire EDM), though the body can be formed from any alternative fabrication process. The fixation bodies 42 and 42' (see FIGS. 8-9) can be constructed from any suitable biocompatible material including but not limited to commercially pure titanium, titanium alloy such as TAN, stainless steel, reinforced plastics, polymers such as polyether ether ketone (PEEK) or PE, and the like.

As illustrated, the fixation body 42 includes five links 46A-E, though any number of links can be used such that reliable fixation can be achieved to a patient's mandible or maxilla, such as three links, four links, or five links. Referring to FIG. 2B, the links 46A-E have a rectangular cross-section that is elongate in the vertical plane defined by the transverse T and longitudinal L directions. Specifically, the links 46A-E include opposed elongate edges 47 and minor edges 49. The elongate edges 47 can have any length as desired, such as about 1 mm while the minor edges 49 can have any length as desired, such as about 0.6 mm. The links 46A-E can define a lateral thickness as desired, such as approximately 0.6 mm in accordance with one embodiment. Of course, it may be desirable to eliminate sharp corners or edges that could cause injury to surrounding tissue when implanted in a patient. The size and shape of the links 46 impart flexibility to the fixation body 42, thereby allowing the fixation body 42 to assume multiple sizes, and also allowing for variable positioning of the fixation device 40 when implanted in the patient. In this regard, it should be appreciated that the links 46A-E can alternatively define any suitable alternative geometric size and shape as desired. One or more of the links 46A-E can be similarly or identically or substantially identically constructed, and will now be described with reference to the link 46B.

In particular, referring again to FIG. 2A, the link 46B includes a pair of opposed first and second side members 48 and 50. Each side member defines respective longitudinally inwardly curved upper ends 52 and 54 and opposed longitudinally outwardly curved lower ends 56 and 58. The upper ends 52 and 54 of the side members 48 and 50 of the link 46B are joined at a first interface 53, so as to form a crest 51 of the fixation body 42. The crest 51 is continuously curved about a laterally extending axis, such that the crest 51 presents a convex surface with respect to a downwardly directed view of the top of the fixation body 42. Of course, it should be appreciated that the crest 51 could assume any alternative shape as defined by the upper ends 52 and 54 of the side members 48 and 50, or as defined by a separate structure that joins the upper ends 52 and 54, either directly or indirectly.

The side members 48 and 50 are longitudinally spaced from each other, and extend linearly so as to flare longitudinally outward from each other along a downward direction from their respective upper ends 52 and 54 to their lower ends 56 and 58 in the illustrated embodiment. Thus, the first side member 48 flares longitudinally outward toward the first outer end 43 of the fixation body 42 in a downward direction along the side member 48. Likewise, the second side member 50 flares longitudinally outward toward the second outer end 45 of the body in a downward direction along the side member 50. In the illustrated embodiment, the side members 48 and 50 flare equally outward with respect to a transverse midline TM of the link 46B at a desired angle θ anywhere between 0° and 90°, for instance between 0° and 45°, such as approximately 14°.

The lower end 56 of the first side member 48 of the link 46B is connected to the lower end 58 of the side member 50 of the adjacent link 46A at a second interface 53 to form a valley 60 of the fixation body 42, and the lower end 58 of the side member 50 of the link 46B is connected to the lower end 56 of the side member 48 of the adjacent link 46C at a third interface 53 to likewise form another valley 60 of the fixation body 42. The valleys 60 are continuously curved about a laterally extending axis, such that the valley presents a convex surface with respect to an upwardly directed view of the bottom of the fixation body 42. Of course, it should be appreciated that the valleys could assume any alternative shape as defined by the lower ends 56 and 58 of the side members 48 and 50, or as defined by a separate structure that joins the lower ends 56 and 58 of adjacent links, either directly or indirectly. The side members 48 and 50 of each link are integrally connected to the complementary side members of the adjacent links at the interfaces 53, though they could alternatively be discreetly attached to each other at the interfaces 53. Furthermore, the side members 48 and 50 can assume any size and shape as desired that connects the crest 51 to the valleys 60, either directly or indirectly.

The fixation body 42 can define any desired longitudinal distance, or width W between adjacent valleys 60, and therefore between adjacent crests 51, such as approximately 20 mm, and any desired transverse height H between the lower edge of the valley 60 and the upper edge of the crest 51, such as approximately 17.6 mm. The fixation body 42 can be configured such that a spatial relationship is defined between the respective crests 51 and/or valleys 60. For example, the spatial relationship can be defined such that the width W between each of the crests 51 and the width W between each of the valleys 60 is uniform throughout the fixation body 42, as illustrated. Alternatively, the spatial relationship can be defined with two or more crests 51 separated by different widths W, two or more valleys 60 separated by different widths W, or any combination thereof. Of course spatial relationships with respect to the height H between the crests 51 and the valleys 60 can also be defined.

It should be appreciated that although the links 46A-E of the illustrated configuration are all the same size and shape, that one or more, up to all of the links 46A-E of the fixation body 42 can have different sizes and/or shapes, for example having different widths W, heights H, or any combination thereof. It should further be appreciated that the links 46A-E need not all have the same cross-section, as defined between the elongate edges 47 and the minor edges 49. For example, it may be desirable to configure one or more of the links 46A-E with different lateral thicknesses, for instance to control the deformation characteristics of particular links when the fixation body 42 is flexed inwardly or outwardly in the longitudinal direction L, or otherwise shaped prior to implantation in a patient, as described in more detail below. Furthermore, the cross section within an individual link can be varied along one or more portions between its respective adjacent valleys 60.

It should be appreciated that the links 46A-E define an undulating fixation body 42 shaped in a wave-form having wave segments that are proportional in number to the number of links 46. While five links 46A-E are illustrated, the fixation body 42 can include any number of links 46A-E as desired. Each link 46A-E is illustrated as defining a crest 51 of the wavelike structure, and a portion of a valley 60 of one or more adjacent wavelike structures. It should also be appreciated that the longitudinal widths W and transverse heights H can vary between adjacent crests and valleys. For instance, one or more of the crests 51 can have a height H greater or lesser than that of one or both of the immediately adjacent crests.

The side member 48 of the outer link 46A disposed at the first end 43 of the fixation body 42 terminates at its lower end 56, while the side member 50 of the outer link 46E disposed at the second end 45 of the fixation body 42 terminates at its lower end 58. Alternatively, it should be appreciated that a half-link could be disposed at the opposed outer ends 43 and 45, such that each half-link would terminate at their respective upper ends 52 and 54, or at any alternative location along their lengths as desired. In the illustrated embodiment, the lower end 56 of the side member 48 of the outer link 46A and the lower end 58 of the side member 50 of the outer link 46E terminate at respective bone attachment locations 70, as will be described in more detail below.

The fixation body 42 includes a plurality of bone attachment locations 70 that facilitate attachment of the fixation body to the underlying bone. For instance, as described above, the fixation body 42 can be attached to an underlying mandible or maxilla, or any alternative bone structure, such that a bone fracture is disposed between the opposed outer ends 43 and 45 of the fixation body 42. Accordingly, in the instance of mandibular or maxillo fixation, when a pair of fixation bodies 42 are secured to each other in the manner described above with respect to FIG. 1, the broken bone segments are relatively immobilized to facilitate healing.

In the illustrated embodiment, the bone attachment locations 70 are provided as screw holes 72 extending laterally through the fixation body 42 at the respective valleys 60, though one or more alternatively configured attachment locations can be provided in any suitable manner so as to facilitate attachment of the fixation body 42 to underlying bone. The screw holes 72 can be sized to threadedly receive corresponding fasteners 44, provided in one embodiment as bone screws 74. Specifically, referring to FIG. 6, the fixation body 42 includes a beveled inner surface 76 that defines each screw hole 72, and is sized and shaped to receive a correspondingly beveled outer surface 78 of a screw head 80. The beveled surface 76 is positioned such that the screw head 80 does not protrude outwardly from the fixation body 42 when fully seated in the screw hole 72. As illustrated, the screw head 80 is flush with the outer surface 59 of the fixation body 42, though the screw head 80 could alternatively be inwardly recessed or slightly outwardly protruding with respect to the outer surface 59 of the fixation body 42.

Figure 6:
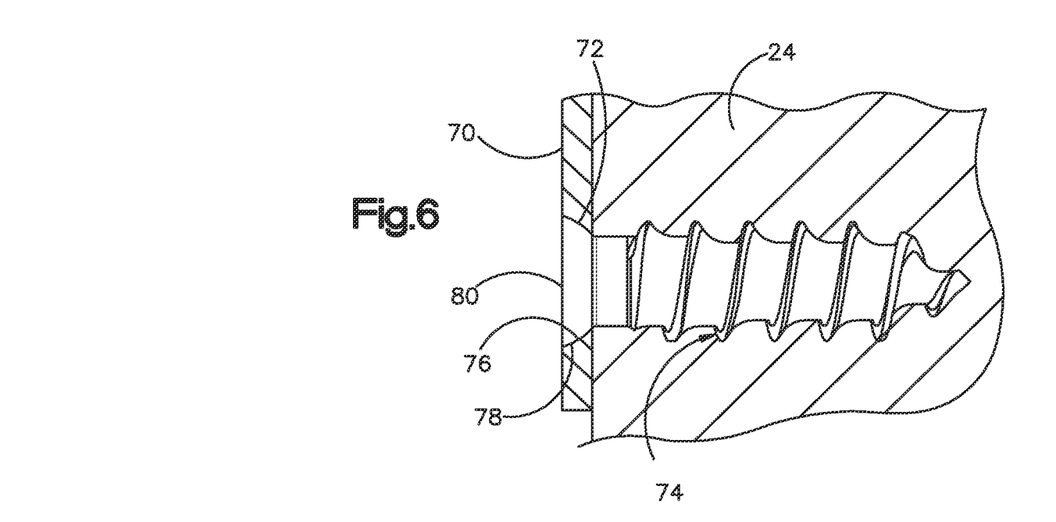
FIG. 6 is a sectional elevation view of the mandibular fixation device illustrated in FIG. 2A, implanted in the manner illustrated in FIG. 1, and taken along line 6-6 of FIG. 1 to show the fixation of the device to the mandible.

Of course, the screw hole 72 could assume one of numerous configurations, such that the inner surface 76 can be beveled straight, or rounded at any desired radius, for instance approximately 3.6 mm. Alternatively still, the inner surface 76 need not be beveled, and can extend laterally in a direction parallel to the outer surface of the screw head 80. As another example, while the inner surface 76 is illustrated as smooth and flat, the inner surface 76 could alternatively be threaded to threadedly engage corresponding threads of the screw head 80, such that the screw 74 would be self-locking within the screw hole 72. It should also be appreciated that the bone screws 74 can be self-drilling, or could alternatively be insertable into a pre-drilled hole as appreciated by one having ordinary skill in the art. The fixation device 40 can further include a collar that surrounds the screw hole 72 at the inner surface 57 of the fixation body 42, such that the collar would be disposed between the fixation body 42 and the underlying bone structure. The collar would thus provide a stand-off that spaces the fixation body 42 from the patient's gum when the bone screws 74 are fully inserted into the underlying bone.

As described above, the links 46A-E are constructed so as to impart a flexibility to the fixation body 42. Specifically, the fixation body can bend about a transverse axis to conform generally with dental arches of patients of different sizes and shapes, thereby allowing the bone screws 74 to be inserted into the screw holes 72 and screwed into an underlying mandible or maxilla, as illustrated in FIG. 1. Furthermore, referring to FIGS. 3A-C, the links 46A-E can allow the fixation body 42 to flex longitudinally.

Figure 3A:
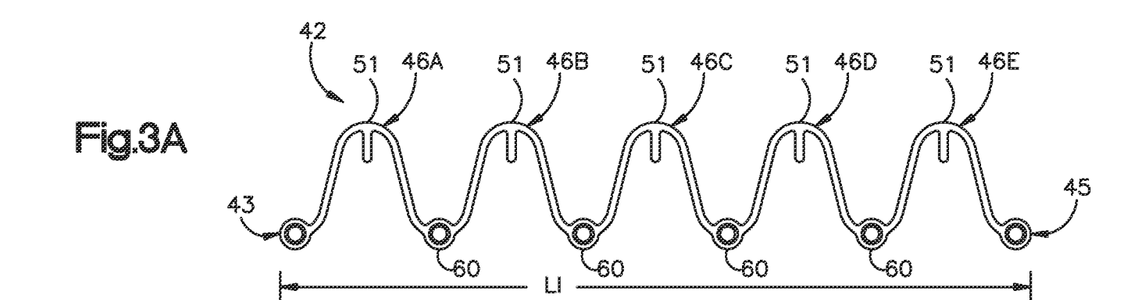
FIG. 3A is a front view of the fixation device illustrated in FIG. 2A in the neutral configuration.

For instance, FIGS. 2A and 3A illustrate the fixation body 42 in an initial relaxed, or neutral configuration, whereby the fixation body is in its as-manufactured configuration prior to inward or outward flexing along the longitudinal direction L. In the neutral configuration, the fixation body 42 can define any longitudinal distance LI as desired between the opposed longitudinally outermost edges, such as approximately 100 mm.

Figure 3B:
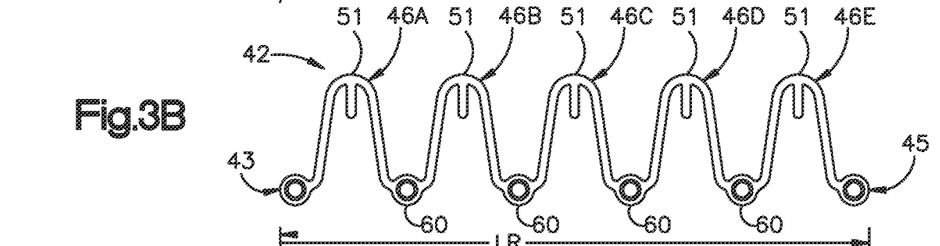
FIG. 3B is a front view of the fixation device illustrated in FIG. 3A, but shown in a compressed configuration.

However, as shown in FIG. 3B, a longitudinally inwardly directed force can be applied to one or more, including all, of the links 46, thereby compressing the crests 51 and/or valleys 60 and achieving a reduced longitudinal length LR of the fixation body 42 to a distance less than the initial distance LI, as desired. The fixation body 42 can be configured such that when the length of the fixation body 42 is adjusted by longitudinal compression, the longitudinal distance, or spacing between the crests 51 and/or valleys 60 (i.e., the width W (FIG. 2A) between adjacent crests 51 and/or valleys 60) in the compressed configuration of the fixation body 42 is preserved with respect to the relaxed or neutral configuration of the fixation body 42. In other words the spacing, or width W between adjacent crests 51 and/or valleys 60 of the fixation body 42 will be smaller after the longitudinal compression, but the crests 51 and/or valleys 60 can maintain their spatial relationship; for instance the crests 51 can still be spaced apart equally as they were in the neutral configuration, and the and valleys 60 can also be spaced apart equally as they were in the neutral configuration.

Figure 3C:
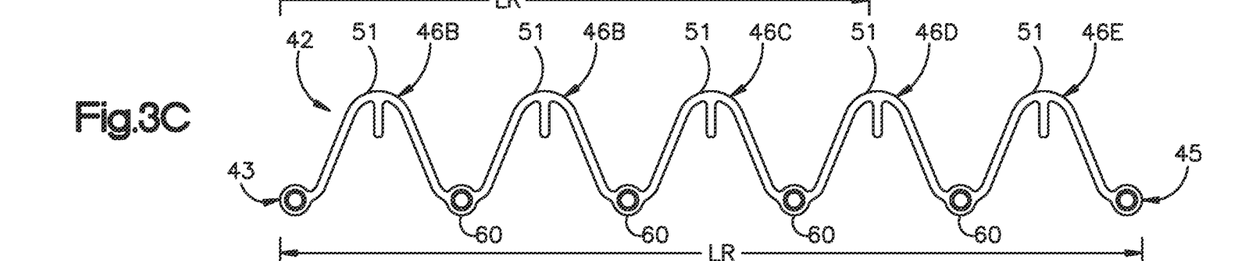
FIG. 3C is a front elevation view of the fixation device illustrated in FIG. 3A, but shown in an expanded configuration.

Additionally, as shown in FIG. 3C, a longitudinally outwardly directed force can be applied to one or more, up to all, of the links 46, thereby extending the crests 51 and/or valleys 60 and achieving an extended, or expanded longitudinal length LE of the fixation body 42 to a distance greater than the initial distance LI, as desired. The fixation body 42 can be configured such that when the length of the fixation body 42 is adjusted by longitudinal expansion, the longitudinal distance, or spacing between the crests 51 and/or valleys 60 (i.e., the width W between adjacent crests 51 and/or valleys 60) in the expanded configuration of the fixation body 42 is preserved with respect to the neutral configuration of the fixation body 42. In other words the spacing, or width W between adjacent crests 51 and/or valleys 60 of the fixation body 42 will be greater after the longitudinal expansion, but the crests 51 and/or valleys 60 can maintain their spatial relationship; for instance the crests 51 can still be spaced apart equally as they were in the neutral configuration, and the and valleys 60 can also be spaced apart equally as they were in the neutral configuration. It should be appreciated that the fixation body 42 can be configured such that the transverse height H between the crests 51 and/or valleys 60 after the fixation body 42 is compressed and/or expanded is similarly preserved with respect to the neutral configuration of the fixation body 42.

It should therefore be appreciated that the bone attachment locations 70 can remain aligned with the underlying bone even as the fixation body 42 is flexed longitudinally inward and/or outward. Furthermore, the bone attachment locations 70 can be aligned or substantially aligned with each other along a longitudinal axis LA even as the fixation body 42 is flexed longitudinally inward and outward. In one embodiment, the fixation body 42 can stretch or compress lengthwise longitudinally an amount between 5% and 50% with respect to its length in the relaxed position, for instance between 10% and 40%, and more particularly between 20% and 30%, and more particularly still about 23%. The fixation body 42 can further stretch or compress height-wise transversely by any suitable percentage with respect to its height in the relaxed position, such as between 1% and 25%, for instance between 5% and 15%, and more particularly about 11%. It should be appreciated that when the body 42 is stretched longitudinally, the body 42 tends to shrink or compress transversely, and vice versa. Furthermore, when the body 42 is compressed longitudinally, the body 42 tends to stretch transversely, and vice versa.

Thus, the configuration of the fixation body 42 can be adjusted in situ while implanting the fixation device 40 in the patient. For instance, the fixation body 42 can be sized and configured as desired based on the size of the underlying bone segments to be fixed. Additionally, the fixation body 42 can be sized and configured to place the connection locations in a desired position prior to fastening the fixation body 42 to underlying bone. Furthermore, the side members 48 and 50 allow the fixation body 42 to be bent or otherwise configured in the vertical plane as well, for instance, when aligning the fixation body 42 with underlying bone. While the fixation body 42 is flexible, the continuity between adjacent links 46 provides sufficient stiffness when the fixation device 40 is affixed to underlying bone and attached to a complementary fixation device in a fixation system.

It should be appreciated that the fixation body 42 can be constructed so as to allow the fixation body 42 to extend and/or compress as desired. In this regard, the fixation body 42 includes at least two side members that are longitudinally spaced from each other by an interface 53 that can expand and compress in response to expansive and compressive forces. As illustrated, the interfaces 53 are curved surfaces (e.g., the crests 51 and valleys 60) whose curvature can be increased and reduced through flexing, though the interfaces 53 can alternatively include angled connections between the side members 48 and 50. The compressive and expansive deformation of the fixation body 42 can be plastic, or can alternatively be elastic such that the deformed shape is retained when the fixation body 42 is attached to the underlying bone at the attachment locations 70. Of course, the height of the fixation body 42 may increase slightly when the fixation body 42 is compressed, and may decrease slightly when the fixation body 42 is extended.

Figure 4:
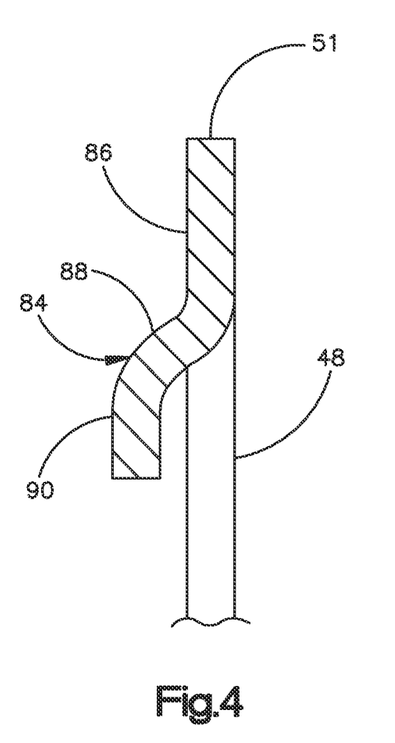
FIG. 4 is a sectional elevation view of the fixation device illustrated in FIG. 2A, taken along line 4-4.

Referring again to FIG. 2A and also to FIG. 4, the fixation device 42 further includes a plurality of connection, or securement locations 82 configured to facilitate connecting, or securing together a pair of fixation devices 40 that are inversely oriented, for instance when implanted in a mandible and maxilla, respectively. In the illustrated configuration, the securement locations 82 are disposed at the longitudinal midpoint, or apex of the crest 51 of each of the links 46A-E. However, it should be appreciated that alternatively, the securement locations 82 can be disposed anywhere on the fixation body 42 as desired. The securement locations 82 can be configured to allow a securement member, such as the securement member 23 described above with respect to FIG. 1, to connect a pair of fixation bodies 42 to each other so as to restrict relative movement of the bone underlying the connected fixation bodies 42.

The securement locations 82 are provided in the illustrated embodiment as tangs 84 extending down from the apex of each crest 51 of the fixation body 42. Otherwise stated, the tangs 84 extend in a generally transverse direction from the crest 51 toward a longitudinal axis LA that extends through the screw holes 72. One or more, up to all, of the tangs 84 can also include longitudinally or laterally extending segments as well, if desired. For instance, in the illustrated embodiment, each of the tangs 84 includes a first segment 86 that extends transversely down from the transverse inner edge of the apex of the crest 51. A second, or spacer segment 88 extends transversely downward and laterally outward from the lower end of the first segment 86. A third segment 90 extends transversely downward from the lower and laterally outer end of the spacer segment 88.

Thus, a securement device, such as the securement device 23 described above, can engage the lower surface of the spacer segment 88 and laterally inner surface of the third segment 90 when fixing or stabilizing a pair of mandibular and maxillo fixation bodies 42 to each other. Alternatively or additionally, the securement device 23 can engage the laterally inner surface of the first segment 86 and the laterally outer surface of the crest 51. For instance, a wire can be wrapped around the tang 84 and/or link 46. Alternatively or additionally, an elastic band can be seated at one end between the tang 84 and the crest 51. Because securement devices 23 can be attached at multiple locations along the length of the fixation body 42, the resulting forces associated with coupling the securement devices 23 to a complementary fixation body 42 distributes the resulting forces substantially equally across the length of the fixation body 42.

Figure 5:
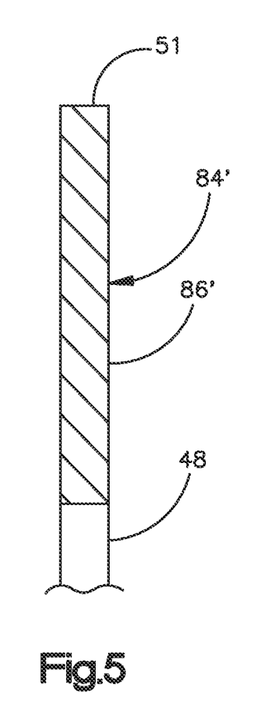
FIG. 5 is a sectional elevation view of the fixation device similar to FIG. 4, but illustrated in accordance with an alternative embodiment.

Alternatively, referring now to FIG. 5, one or more, up to all, of the tangs 84' can include a single segment 86' constructed similarly with respect to the segment 86, thus extending vertically down from the crest 51 in the manner describe above. Thus the tang 84' does not include any lateral or longitudinal directional components. The securement device 23 can be wrapped around the segment 86' in the case of a wire, for instance, or can be seated between the segment 86' and the crest 51 in the case of an elastic band. Alternatively still, it should be appreciated that the securement locations 82 can include the crest 51 itself, without any tangs 84 or other additional structure. For instance, a plurality of elastic bands could be slid along the wavelike form of the fixation body 42 to locations at respective crests 51 prior to implantation of the fixation body 42 into underlying bone. Alternatively, a wire could be wrapped around the crests 51 of opposed fixation bodies 51 prior to or after implantation of the fixation bodies 42. Alternatively still, the securement location 82 could be provided as an aperture extending laterally through the links 46A-E, for instance at their crests 51.

The fixation device 40 was illustrated and described above in accordance with one embodiment, it being appreciated that numerous alternative embodiments are contemplated.

Figure 7:
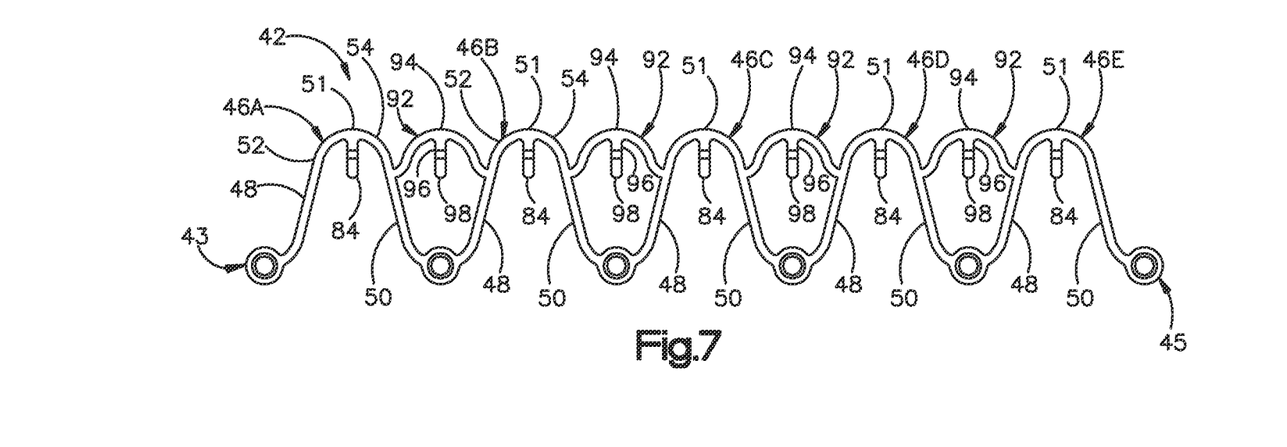
FIG. 7 is a front elevation view of a bone fixation body constructed in accordance with an alternative embodiment.

For instance, referring to now FIG. 7, the fixation body can include auxiliary links, and can alternatively or additionally include securement locations that are positioned differently than the securement locations 82 described above. As illustrated in FIG. 7, the fixation body 42 can include auxiliary links 92 connected between adjacent links 46. The auxiliary links 92 can extend between the first and second side members 48 and 50 of adjacent links 46 at any respective desired locations along the first and second side members 48 and 50, respectively. For instance, in the illustrated embodiment, the auxiliary links 92 extend between the first and second side members 48 and 50 at locations proximate to, or at, the respective upper ends 52 and 54 of the first and second side members 48 and 50. The auxiliary links 92 are illustrated as extending transversely upward and inward from the side members 48 and 50 toward an auxiliary crest 94 that is shaped substantially as described above with respect to the crests 51. Thus, the auxiliary crest 94 presents a convex surface with respect to a downwardly directed view of the top of the fixation body 42, though the auxiliary crest 94 could assume any alternative shape as desired. The auxiliary crests 94 allow the auxiliary links 92 to expand and contract as described above with respect to FIGS. 3A-C, though the auxiliary links 92 can be configured to add an amount of stiffness to the fixation body 42 with respect to the fixation body 42 as illustrated in FIG. 2A without the auxiliary links 92. The auxiliary crests 94 can be positioned longitudinally midway between the crests 51 of the links 46A-E, which can be referred to as "primary" links 46A-E when the fixation body 42 includes the auxiliary links 92.

As illustrated in FIG. 7, one or more, up to all of the auxiliary links 92 can be configured as auxiliary securement locations 96, constructed differently or as described above with respect to the securement locations 82. The auxiliary securement locations 96 can be provided anywhere along the auxiliary links 92, such as at the apexes of the auxiliary crests 94. Thus, for instance, the auxiliary securement locations 96 can be configured to allow a securement member, such as the securement member 23 described above with respect to FIG. 1, to connect a pair of fixation bodies 42 to each other so as to restrict relative movement of the bone underlying the connected fixation bodies 42. In the illustrated embodiment, the auxiliary securement locations 96 are provided as tangs 98 that extend from the auxiliary crests 94 as described above with respect to tangs 84 and 84' extending from respective crests 51. It should be appreciated that the auxiliary securement locations 96 can be provided in addition to the securement locations 82, as an alternative to the securement locations 82, or that any combination of the securement locations 82 and/or the auxiliary securement locations 96 can be provided as desired.

Figure 8:
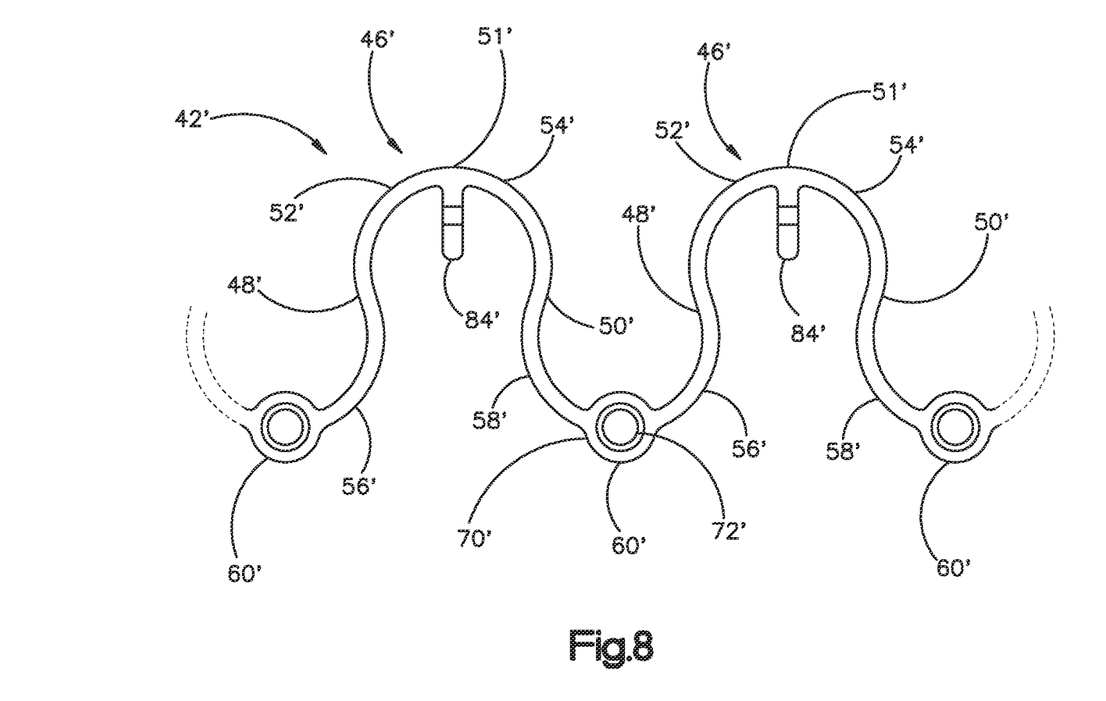
FIG. 8 is a front elevation view of a bone fixation body constructed in accordance with another alternative embodiment.

Referring now to FIG. 8, a portion of a fixation body 42' is illustrated as including a plurality of links 46' that are shaped differently with respect to the straight side members 48 and 50 of the links 46A-E illustrated in FIG. 2A. For instance, as illustrated, the side members 48' and 50' of a given link 46' can be longitudinally inwardly curved toward each other from their respective lower end 56' and 58' near their respective valleys 60' in a transverse upward direction along the side members 48' and 50' toward the crest 51', then longitudinally curved outwardly away from each other in a continuing transverse upward direction, and finally longitudinally curved inwardly toward each other again at the respective upper ends 52' and 54' of the side members 48' and 50' near the crest 51'. It should be appreciated that the illustrated curvature of the side members 48' and 50' is an example of alternative curvature for the links 46', and that the side members 48' and 50' can be configured with any other alternative curvature as desired. It should further be appreciated that the fixation body 42 of a fixation device 40 can be configured entirely of links 46', thereby providing a fixation body 42', or can be configured with any combination of the links 46' and the links 46 as described above with reference to FIGS. 2A-B, as desired. The curved side members 48' and 50' can be configured to allow the fixation body 42' to flex in the transverse direction. Accordingly, when a pair of fixation devices 40 having fixation bodies 42' are secured to each other as illustrated in FIG. 1, the fixation devices 40 can flex toward each other in response to the forces applied by the securement device 23. It should be appreciated that the fixation body 42' can further include auxiliary links and/or auxiliary securement locations as described above with reference to FIG. 7.

Figure 9:
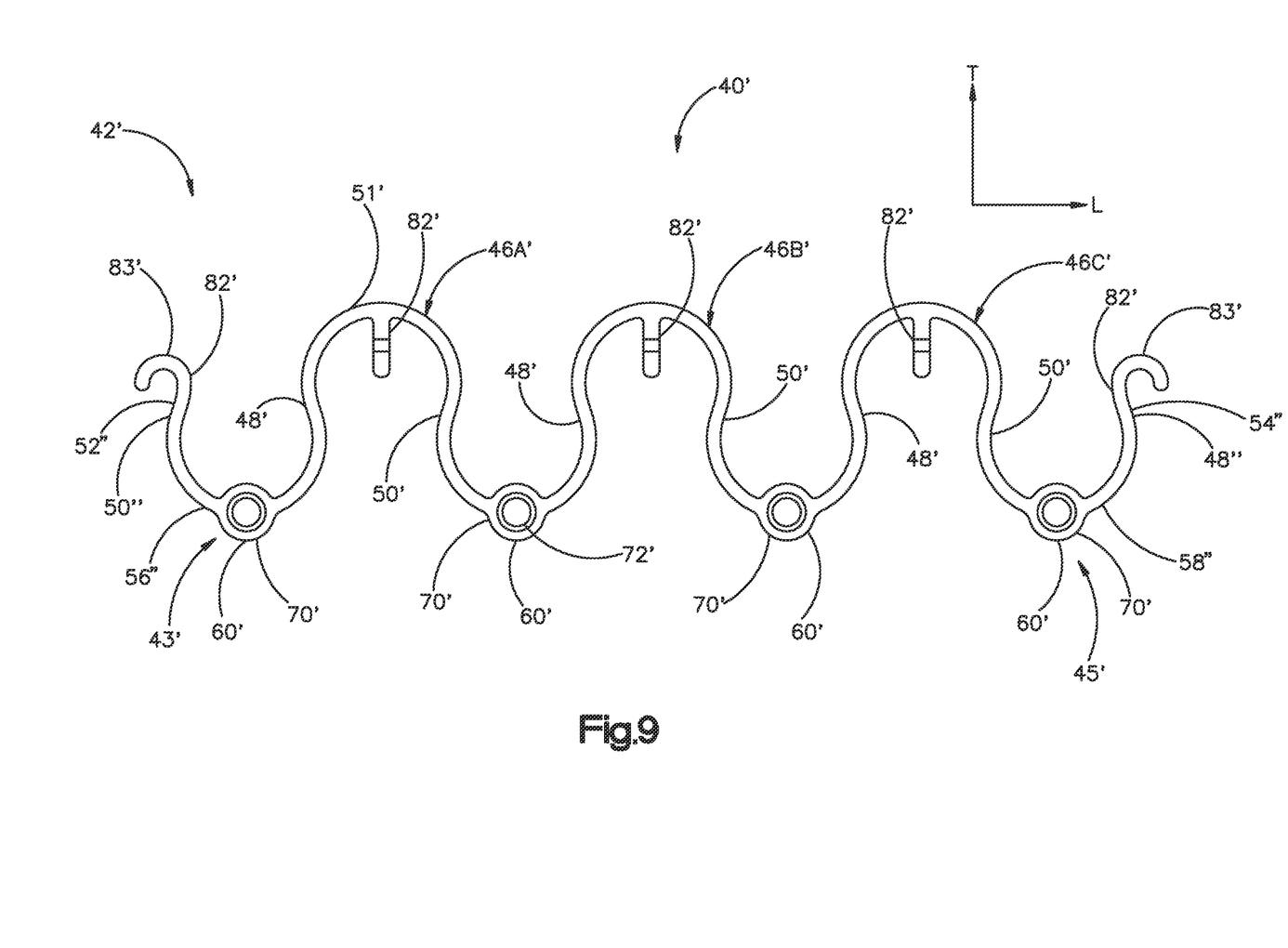
FIG. 9 is a front elevation view of a bone fixation body constructed in accordance with another alternative embodiment.

Furthermore, as described above, the lower end 56 of the side member 48 of the outer link 46A and the lower end 58 of the side member 50 of the outer link 46E terminate at respective bone attachment locations 70, as illustrated in FIG. 2A. Accordingly, as illustrated in FIG. 2A, the bone fixation device 40 can terminate at outermost bone attachment locations 70. Alternatively, as illustrated in FIG. 9, in which the bone fixation device 40' includes three links 46A'-C', the outermost links 46A' and 46C' are attached to outermost securement locations 82' via arms 50'' and 48'', respectively. The arms 50'' and 48'' extend longitudinally outwardly from the ends 43' and 45' of the fixation body 42', between lower arm ends 56'' and 58'' and upper arm ends 52'' and 54'', respectively. However, it should be appreciated that the bone fixation device 40' as illustrated in FIG. 9 could be constructed as described above with reference to FIG. 2A, or any alternative embodiments described herein. Thus, the outermost securement locations 82' are disposed longitudinally outward with respect to the outermost bone attachment locations 70'. As illustrated, the fixation body 42' can include four bone attachment locations 70' as illustrated, or any alternative number of bone attachment locations 70' as desired. The outermost securement locations 82' can be disposed above, below, or at a transverse height substantially equal to that of the other securement locations 82' of the bone fixation device 40'. In the illustrated embodiment, the outermost securement locations 82' are disposed at a transverse height below that of the other securement locations 82' of the bone fixation device 40'.

The outermost securement locations 82' can be provided as hooks 83' extending in the longitudinal-transverse plane, or any alternative plane as desired, for example from the upper arm ends 52'' and 54'' of the arms 50'' and 48'', respectively. Thus, a securement device, such as device 23 described above, can engage the hooks 83' of opposed fixation bodies 42' when fixing or securing a pair of mandibular and maxillo fixation bodies 42' to each other. In this regard, it should be appreciated that any of the securement locations described herein could comprise hooks or any alternative structure suitable for connecting, or securing a pair of fixation devices as described above.

Thus, it should be appreciated that fixation bodies can be provided in accordance with multiple embodiments. Therefore, a kit can be provided that includes a plurality of fixation devices, or portions thereof, including fixation bodies constructed in accordance with all or a portion of any of the embodiments described herein. For example, the kit can include one or more fixation bodies 42 or 42', having different numbers of links, different dimensions, such as overall length, link width, height, and lateral thickness, and differently configured links (for instance differently configured side members 48, 48', 50, and 50', securement locations 82, 82', and 96, and/or auxiliary links 92). Therefore, the fixation bodies in a kit can have one or more varying characteristic such as size and/or shape. For instance, a first kit can be provided having one or more fixation bodies whose components, for instance the links and/or the securement locations, are of a first size or shape, and other fixation bodies whose components are of a second size or shape different than the first size or shape. Thus, the kit can accommodate multiple maxillo-mandibular fixation procedures involving substantial anatomical variability.

According to another embodiment, methods are provided for implanting the various embodiments of the fixation device 40. Generally, the methods include the steps of adjusting an orientation (e.g., directional or angular) of the fixation device 40 depending on the anatomy of the underlying bone structure. For instance, a maxillo fixation device will be vertically inverted with respect a mandibular fixation device. It is to be understood that certain steps of the methods described herein can be omitted, combined, performed simultaneously, or performed in a different order. In this regard, it should be appreciated that the maxillo-mandibular fixation devices of the type described above can be provided as a kit that is configured to be implemented for the purposes of maxillo-mandibular fixation using the methods described below.

According to one method of providing fixation to a bone or bone segments of a mandible, a first fixation device such as the fixation device 40 may be adapted by imparting a curvature as desired to correspond to the dental arch. The fixation device 40 can further be extended or compressed in the longitudinal direction and/or the transverse direction to align the screw holes 72 with a desired fixation location on the underlying bone. Thus the configuration of the fixation body 42 may be adapted to achieve the proper shape and fit for a bone fixation. The fixation body 42 can then be implanted by inserting the fasteners 44 into the underlying bone.

Next, a second fixation device 40 can be implanted in a second bone structure that is to be fixed with respect to the bone structure that underlies the first fixation body 40. For instance, a second fixation body 42 can be implanted into the maxilla in the manner described above, but in an orientation that is vertically inverse with respect to the first fixation device 40. It should be appreciated that either the first and/or second fixation device is implanted over a fracture such that the device(s) attach a first bone segment to a second bone segment that has been fractured from the first bone segment.

Once the first and second fixation bodies are implanted into the underlying bone structure, the securement devices 23 are attached to the securement locations of the first and second fixation bodies. In a preferred embodiment, the securement devices 23 are attached between two vertically aligned, or substantially aligned, crests 51. It should be appreciated that the crests 51 of each fixation body can define the shortest vertical distance between the fixation bodies 40, thereby allowing for a securement device 23 that has a short length between the fixation bodies 40.

The illustrated embodiments are directed to a bone fixation system that may be implanted to assist in repairing a fractured bone. The fixation system has particular utility as mandibular or maxillo fixation system, which benefits from accurate anatomical shape and fit.

The foregoing description is provided for the purpose of explanation and is not to be construed as limiting the invention. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the invention is not intended to be limited to the particulars disclosed herein. Moreover, any of the embodiments described above can incorporate any structures or features of any of the other embodiments described above, as desired. Those skilled in the relevant art, having the benefit of the teachings of this specification, may effect numerous modifications to the invention as described herein, and changes may be made without departing from the spirit and scope of the invention as defined by the appended claims.

What is claimed:

1. A maxillo-mandibular fixation kit comprising:
   a first bone fixation body including a first plurality of interconnected links adjacent to each other along a respective first longitudinal direction between opposed first and second ends of the first bone fixation body, the first plurality of links defining a plurality of crests and an opposed plurality of valleys configured so that the first bone fixation body has an undulating shape,
   the first bone fixation body including 1) a first plurality of bone attachment locations, each of the first plurality of bone attachment locations defined at a respective one of the first plurality of valleys, and 2) a first plurality of securement locations, each of the first plurality of securement locations defined at a respective one of the first plurality of crests, wherein the links of the first plurality of links are flexible in the longitudinal direction such that a length of the first bone fixation body defined from the first end to the second end is adjustable along the longitudinal direction; and
   a second bone fixation body including a second plurality of interconnected links extending in a respective second longitudinal direction between opposed first and second ends of the second bone fixation body, the second plurality of links defining a plurality of crests, a plurality of valleys, a second plurality of bone attachment locations, and a second plurality of securement locations, wherein the links of the second plurality of links are flexible in the second longitudinal direction;
   wherein the first and second pluralities of securement locations are configured to engage with a securement device that fixes the first bone fixation body with respect to the second bone fixation body.

2. The maxillo-mandibular fixation kit as recited in claim 1, wherein the second bone fixation body differs from the first bone fixation body according to at least one of the following:
   the second plurality of interconnected links has a different quantity of links than the first plurality of interconnected links;
   the second plurality of bone attachment locations has a different quantity of bone attachment locations than the first plurality of bone attachment locations;
   the second plurality of bone attachment locations is spaced differently than the first plurality of bone attachment locations;
   the second plurality of securement locations has a different quantity of securement locations than the first plurality of securement locations;
   the links of the second plurality of interconnected links have a different shape than the links of the first plurality of interconnected links;
   the first bone fixation body further includes a plurality of auxiliary links extending between respective crests of the first plurality of interconnected links; and
   the second bone fixation body further includes a plurality of auxiliary links extending between respective crests of the second plurality of interconnected links.

3. The kit of claim 1, wherein the first bone fixation body is configured for attachment to a maxilla and the second bone fixation body is configured for attachment to a mandible.

4. The maxillo-mandibular fixation kit as recited in claim 1, wherein the first plurality of bone attachment locations are spaced apart from each other along the first longitudinal direction.

5. The maxillo-mandibular fixation kit as recited in claim 1, wherein the second plurality of bone attachment locations are spaced apart from each other along the second longitudinal direction.

6. The maxillo-mandibular fixation kit as recited in claim 1, wherein the links of the second bone fixation body are flexible in the second longitudinal direction such that a length of the second bone fixation body defined from the first end to the second end is adjustable along the second longitudinal direction.

7. The maxillo-mandibular fixation kit as recited in claim 1, wherein at least one of the bone attachment locations of the first and second bone fixation bodies is configured to receive a respective bone fastener so as to attach the corresponding one of the first and second bone fixation bodies to underlying bone.

8. The maxillo-mandibular fixation kit as recited in claim 7, further comprising the bone fastener.

9. The maxillo-mandibular fixation kit as recited in claim 8, wherein the bone fastener is a bone screw.

10. The maxillo-mandibular fixation kit as recited in claim 7, further comprising a plurality of bone screws each configured to be inserted into a respective one of the bone attachment locations of the first and second bone fixation bodies.

11. The maxilla-mandibular fixation kit as recited in claim 1, further comprising the securement device.

12. The maxilla-mandibular fixation kit as recited in claim 11, wherein the securement device comprises at least one of a wire and an elastic band.

13. The maxilla-mandibular kit as recited in claim 1, wherein each of the second plurality of bone attachment locations is defined at a respective one of the plurality of valleys of the second plurality of links, and each of the second plurality of securement locations is defined at a respective one of the plurality of crests of the second plurality of links.

* * * * *